United States Patent [19]

Lyle et al.

[11] Patent Number: 5,028,715

[45] Date of Patent: Jul. 2, 1991

[54] RADIOPROTECTIVE AGENTS AND THEIR METHOD OF MANUFACTURE

[75] Inventors: Robert E. Lyle; William A. McMahon; Donald J. Mangold; Nollie F. Swynnerton, all of San Antonio, Tex.

[73] Assignee: Southwest Research Institute, San Antonio, Tex.

[21] Appl. No.: 306,922

[22] Filed: Feb. 6, 1989

[51] Int. Cl.$^5$ ............................................ C07D 277/04
[52] U.S. Cl. .................................. 548/193; 548/190; 548/365
[58] Field of Search ............... 514/365, 917; 548/200, 548/190, 193

Primary Examiner—Stanley J. Friedman
Assistant Examiner—Zohreh A. Fay

[57] ABSTRACT

A radioprotective agent consisting essentially of 3-(3''-aminoalkyl)-2-arylthiazolidine or a pharmacologically acceptable salt thereof having the formula:

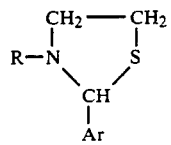

wherein R is a NH$_2$R' or XNHR' radical in which R' is a C$_2$ to C$_4$ alkyl group and X is a C$_1$ to C$_3$ alkyl group and Ar is an aromatic aldehyde moiety; or a pharmacologically acceptable salt thereof.

11 Claims, No Drawings

RADIOPROTECTIVE AGENTS AND THEIR METHOD OF MANUFACTURE

BACKGROUND OF THE INVENTION

This invention was made under United States Government Contract No. DAMD-17-82-C-2075 and the United States Government has a nonexclusive, nontransferable, irrevocable, paid-up license to practice, or have practiced for or on behalf of the United States, this invention throughout the world.

Concern with damage caused by exposure of animals, including humans, to radioactivity has led to increased interest in compounds that can be used by animals to protect them.

Since the initiation of the atomic era several thousand compounds, mainly sulfur-containing, have been synthesized and tested to determine their radioprotective effect. A number of them are known which, if administered prior to exposure to radioactivity, will prolong the life of animals, and by analogy, humans exposed to such radiation. A number of theories have been proposed for this effect, but the precise reasons for the protection against what could be lethal levels of radiation are not completely understood.

Among the different types of compounds which have shown activity are those containing the sulfhydryl group, such as cysteamine or the other aminoalkylthiols and those, such as cysteine, which may be decarboxylated to form aminoalkylthiols. Others include disulfides and trisulfides, organic thiosulfates, phosphorothioates, thioureas and thiazolines. In some instances, ingestion of iodine or some form thereof, such as potassium iodide, can prevent thyroid damage to humans exposed to levels of radioactive iodine and this, in fact, was utilized to treat many humans in Europe when the Chernobyl nuclear incident occurred.

While all of these compounds are somewhat suitable, they are not as satisfactory as would be desired since their metabolism is uncertain in the body and, consequently, they do not give the degree of protection desired. At the present time it is believed that the most effective antiradiation agent is WR 2721; namely, S-(2-(3-aminopropylamino)ethyl phosphorothioate. Such compound, however, is not active by oral dosage. Attempts to make it more suitable for widespread usage as by oral dosage have not been successful.

SUMMARY OF THE INVENTION

The present invention provides novel compounds which will result in active radioprotective properties when administered to animals and to the process of making such products.

Briefly, the present invention is directed to reacting S-(2-(3-aminoalkylamino)ethyl phosphorothioate with an aromatic aldehyde in an alcohol or dimethylsulfoxide medium to form the corresponding thiazolidine. The invention also includes the novel arylthiazolidines and their use as radioprotective agents since, when metabolized by an animal, they will form certain thiols such as 2-(3-aminopropylamino)ethanethiol (WR 1065) which is an active form of WR 2721 in the body of animals, and to the method of protecting animals against the effect of radioactivity utilizing the novel arylthiazolidines.

DETAILED DESCRIPTION

The essential aspect of the instant process is the reaction between a substituted phosphorothioic acid such as WR 2721 and an aromatic aldehyde. While WR 2721 has the formula $H_2NCH_2CH_2CH_2NHCH_2CH_2SPO_3H_2$, the present invention also applies to substituted phosphorothioic acids of the formula:

$$R-NCH_2CH_2SPO_3H_2$$

wherein R is a $NH_2R'$ or $XNHR'$ radical in which $R'$ is a $C_2$ to $C_4$ alkyl group and X is a $C_1$ to $C_3$ alkyl group.

As to the aromatic aldehyde, it can be any of the general formula:

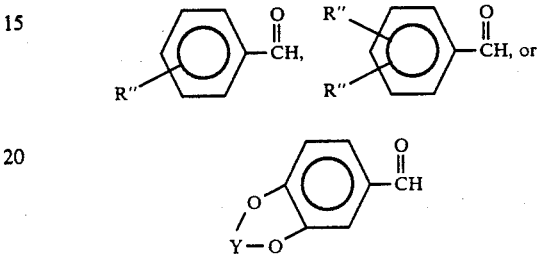

wherein $R''$ is a halogen or nitro, $C_1$ to $C_3$ alkoxy, or $C_1$ to $C_3$ alkyl radical, and Y is a $C_1$-$C_3$ alkylene radical. Specific examples are m-methoxybenzaldehyde, p-nitrobenzaldehyde, p-methoxybenzaldehyde, 3,4-dimethoxybenzaldehyde, and 3,4-(methylenedioxy)benzaldehyde.

The reaction results in a 3-(3'-aminoalkyl)-2-arylthiazolidine of the general formula:

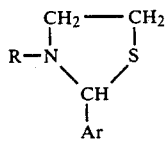

wherein R is a $NH_2R'$ or $XNHR'$ radical in which $R'$ is a $C_2$ to $C_4$ alkyl group and X is a $C_1$ to $C_3$ alkyl group and Ar is the aromatic aldehyde moiety set forth above.

While the generic formula is for the free base, if desired, the pharmacologically acceptable salts of the thiazolidines can be prepared such as the sulfate, hydrochloride, alkyl phosphate and ammonium phosphate and the like. This is accomplished in any conventional manner such as by treating an ether solution of the thiazolidine with the respective anhydrous acid.

These thiazolidines can be metabolized in the body of an animal to thiols, such as 2-(3-aminopropylamino)ethanethiol (WR 1065) which is the active form of WR 2721.

The reaction, as noted, is preferably carried out in the presence of an alcohol in which the substituted phosphorothioic acid is soluble, or in a dimethylsulfoxide medium. The alcohol can be ethanol, methanol, 2-propanol, and the like and the dimethylsulfoxide (DMSO), if utilized, is preferably hydrated to solubilize the WR 2721.

The reaction can be carried out at ambient temperatures and pressures; although, it has been found that reaction goes more rapidly at a temperature of 40 to 60° C.

The thiazolidines are radioprotective agents and can be administered to animals where there is fear of exposure to radioactivity or actual exposure to radiation to mitigate the effects of such radiation. Obviously, the dosage level should be an amount effective to protect against the effects of radiation; ordinarily about 300 mg/kilogram of body weight of the animal. The dosage level will vary from such amount dependent upon many factors such as the particular animal, state of health of the animal, and level of radioactivity to which the animal has been exposed. The dosage level will also vary dependent upon the particular agent used since some are more toxic than others.

The invention will be further described in connection with the following examples which are set forth for purposes of illustration only.

A series of five reactions were carried out in which WR 2721 was reacted with five different aldehydes as set forth more particularly below. In four of the reactions the solvent was alcohol and in the fifth it was DMSO·H$_2$O. These were then tested as set forth in Example 6.

EXAMPLE 1

Preparation of
2-(4'-Nitrophenyl)-3-(3''-aminopropyl)thiazolidine Monoethylphosphate (Radioprotective Agent A)

A suspension of 1.0 g of WR 2721 in a solution of 0.53 g of p-nitrobenzaldehyde in 70 mL of ethanol was heated and stirred for 48 hours. The solvent was removed by evaporation on the rotary evaporator, and The residue was washed several times with ethyl ether. The residue was dried on a rotary evaporator, and the glassy residue was subjected to low pressure drying overnight at 0.5 torr. The resultant product (Radioprotective Agent A) crystallized on treatment with chloroform and the solid product, mp 122–126°, gave spectra identical with those obtained from the oil.

Anal. Calcd for C$_{14}$H$_{24}$N$_3$O$_6$PS: C, 42.74; H, 6.15; N, 10.68. Calcd for C$_{14}$H$_{24}$N$_3$O$_6$PS·½H$_2$O: C, 41.79; H, 6.26; N, 10.44. Found: C, 42.06; H, 6.31; N, 10.40.

EXAMPLE 2

Reaction of WR 2721 with p-methoxybenzaldehyde in Water-Dimethylsulfoxide to give
2-(4'-methoxyphenyl)3-(3''-aminopropyl)thiazolidine Phosphate (Radioprotective Agent B)

A mixture of 1 g WR 2721, 0.55 g of p-methoxybenzaldehyde, 43 g of water, and 14.5 g of dimethylsulfoxide was stirred. After about 40 min, the mixture became homogeneous and stirring was continued for 5 hours. The reaction mixture was poured into 450 mL of acetone and allowed to stand overnight while cooling. The precipitate which formed was removed by filtration and was washed with chloroform and dried to give 0.33 g of a solid, mp 145–149°. The solid was purified by dissolving it in water and precipitating with acetone to give the phosphate salt (Radioprotective Agent B).

Anal Calcd for C$_{13}$H$_{23}$N$_2$O$_5$PS: C, 44.57; H, 6.62; N, 7.99. Calcd for C$_{13}$H$_{23}$N$_2$O$_5$PS·½H$_2$O: C, 43.45; H, 6.90; N, 7.79. Found: C, 43.26, 43.23; H, 6.64, 6.73; N, 7.85.

A small sample of Radioprotective Agent B was dissolved in water, neutralized with sodium carbonate solution and extracted into chloroform. Evaporation of the chloroform gave a residue, the $^1$H NMR of which showed it to be the base of Agent B mixed with a small amount of impurity, probably p-methoxybenzaldehyde or the imine of WR 1065, the hydrolysis product of WR 2721.

EXAMPLE 3

Preparation of
2-(3',4'-Dimethoxyphenyl)-3-(3''-aminopropyl)thiazolidine Monoethylphosphate (Radioprotective Agent C)

A suspension of 2.0 g of WR 2721 in a solution of 1.24 g of 3,4-dimethoxybenzaldehyde in 140 mL of absolute ethanol was stirred at reflux for 48 hours. The clear solution was filtered, and the solvent was removed on a rotary evaporator to yield a glassy residue which was washed with 50 mL of ether. The residue was dissolved in 5 mL of CHCl$_3$, and the product was precipitated by the addition of 125 mL of ether. The ether layer was decanted and the residue, after drying, was dissolved in 5 mL of acetone and again precipitated by the addition of 125 mL of ether. The ether was decanted, and the glassy residue was dried overnight at 0.5 torr to yield 2.61 g of a glassy amorphous solid which was Radioprotective Agent C.

Anal. Calcd for C$_{16}$H$_{29}$N$_2$O$_6$PS: C, 47.05; H, 7.16; N, 6.86. Calcd C$_{16}$H$_{29}$N$_2$O$_6$PS·½H$_2$O: C, 46.03; H, 7.24; N, 6.71. Found: C, 45.96; H, 7.51; N, 6.83. After drying at mp: C, 46.08; H, 7.10.

EXAMPLE 4

Preparation of
2-[3',4'-(Methylenedioxy)phenyl]-3-(3''-aminopropyl)-thiazolidine Monoethylphosphat (Radioprotective Agent D)

A suspension of 2.0 g of WR 2721 in a solution of 1.12 g piperonal in 140 mL of absolute ethanol was stirred at reflux for 48 hours. The clear solution was filtered, and the solvent removed on a rotary evaporator to yield a glassy residue which was dissolved in 5 mL of CHCl$_3$ and precipitated by the addition of 125 mL of ether. The ether layer was decanted and the residue, after drying, was dissolved in 5 mL of acetone and again precipitated by the addition of 125 mL of ether. The ether was decanted, and the glassy residue dried overnight at 0.5 torr to yield 2.05 g of a glassy amphorous solid which was Radioprotective Agent D.

Anal Calcd for C$_{15}$H$_{25}$N$_2$O$_6$PS: C, 45.91; H, 6.42; N, 7.14. Calcd for C$_{15}$H$_{25}$N$_2$O$_6$PS·½H$_2$O: C, 44.88; H, 6.53; N, 6.98. Found: C, 45.54; H, 6.32; N, 6.90.

EXAMPLE 5

Preparation of
2-(3'-Methoxyphenyl)-3-(3''-aminopropyl)thiazolidine Monoethylphosphate (Radioprotective Agent E)

A suspension of 1.0 g of WR 2721 in a solution of 0.48 g of m-methoxybenzaldehyde in 70 mL of ethanol was heated and stirred for 48 hours. The solvent was removed by evaporation on the rotary evaporator, and the residue was washed several times with ethyl ether. The residue was dried under reduced pressure to give the product, Radioprotective Agent D, as a glassy residue. The $^1$H NMR spectrum was consistent with the structure thereof.

Anal. Calcd for C$_{15}$H$_{27}$N$_2$O$_5$PS: C, 47.62; H, 7.18; N, 7.43. Calcd for C$_{15}$H$_{27}$N$_2$O$_5$PS·½H$_2$O: C, 46.51; H, 7.27; N, 7.23. Found: C, 47.30; H, 7.53; N, 7.62.

EXAMPLE 6

Radioprotective Agents A, B, C, and D were tested for acute toxicity and radioprotective activity using test mice at various dosage levels against LD$_{100}$ of γ-radiation. The agents were administered interperitoneally (ip). The results are set forth in Tables I and II that follow.

TABLE I
SUMMARY OF ACUTE TOXICITY OF SUBMITTED COMPOUNDS

| Radioprotective Agent | Vehicle | Drug Dose mg/kg | Route | Deaths | Survivors (%) |
|---|---|---|---|---|---|
| A | H$_2$O | 600 | ip | 5/5 | 0 |
|   |      | 300 | ip | 2/5 | 60 |
|   |      | 150 | ip | 0/5 | 100 |
|   |      | 75  | ip | 0/5 | 100 |
| B | H$_2$O | 600 | ip | 5/5 | 0 |
|   |      | 300 | ip | 5/5 | 0 |
|   |      | 150 | ip | 4/5 | 20 |
|   |      | 75  | ip | 0/5 | 100 |
| C | H$_2$O | 300 | ip | 5/5 | 0 |
|   |      | 150 | ip | 5/5 | 0 |
|   |      | 75  | ip | 5/5 | 0 |
|   |      | 37.5| ip | 0.5  | 100 |
| D | H$_2$O | 300 | ip | 5/5 | 0 |
|   |      | 150 | ip | 5/5 | 0 |
|   |      | 75  | ip | 5/5 | 0 |
|   |      | 37.5| ip | 0/5 | 100 |

TABLE II
SUMMARY OF RADIOPROTECTIVE ACTIVITY OF SUBMITTED COMPOUNDS (1000 RAD)

| Radioprotective Agent | Vehicle | Route | Time Before RAD (min) | Drug Dose mg/kg | Drug Related Lethality | Survivors (%) |
|---|---|---|---|---|---|---|
| A | H$_2$O | ip | 30 | 300 | 5/10 | 40 |
|   |       |    |    | 150 | 0/10 | 30 |
|   |       |    |    | 75  | 0/10 | 20 |
| A | H$_2$O | po | 30 | 1200 | 7/10 | 0 |
|   |       |    |    | 600  | 0/10 | 0 |
|   |       |    |    | 300  | 0/10 | 0 |
| B | H$_2$O | ip | 30 | 75    | 0/10 | 20 |
|   |       |    |    | 37.5  | 0/10 | 0 |
|   |       |    |    | 18.75 | 0/10 | 0 |
|   |       |    |    | 0     | 0/20 | 0 |
| C | H$_2$O | ip | 30 | 435  | 5/5 | 0 |
|   |       |    |    | 217  | 5/5 | 0 |
|   |       |    |    | 109  | 5/5 | 0 |
|   |       |    |    | 54.3 | 0/5 | 100 |
| D | H$_2$O | ip | 0  | 441   | 5/5 | 0 |
|   |       |    |    | 220.6 | 5/5 | 0 |
|   |       |    |    | 110.3 | 5/5 | 0 |
|   |       |    |    | 55.1  | 0/5 | 100 |

The results show that RAdioprotective Agents A and B are toxic at the levels used in this test. Agents C and D showed complete protection at a dose level near the LD$_{50}$ (50 mg/kg) for all the mice survived an LD$_{100}$ dose of irradiation.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A radioprotective agent 3-(3''-aminoalkyl)-2-aryl-thiazolidine or a pharmacologically acceptable salt thereof having the formula:

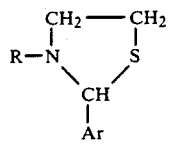

wherein R is a NH$_2$R' or XNHR' radical in which R' is a C$_2$ to C$_4$ alkyl group and X is a C$_1$ to C$_3$ alkyl group and Ar is an aromatic group derived from the corresponding aromatic aldehyde; or a pharmacologically acceptable salt thereof.

2. The agent of claim 1 wherein said aromatic aldehyde is selected from:

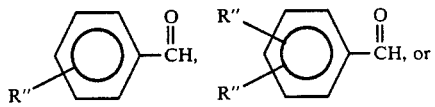

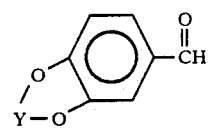

wherein R'' is a halogen or nitro group, C$_1$ to C$_3$ alkoxy, or C$_1$ to C$_3$ alkyl radical, and Y is a C$_1$–C$_3$ alkylene radical.

3. The radio protective agent of claim 1 or 2 wherein said radioprotective agent is selected from 2-(4'-nitrophenyl)-3-(3''-aminopropyl)thiazolidine, 2-(4'-methoxyphenyl)-3-(3''-aminopropyl)thiazolidine, 2-(3',4'-dimethoxyphenyl)-3-(3''-aminopropyl)thiazolidine, 2-[3',4'-(methylenedioxy)phenyl]-3-(3''-aminopropyl)thiazolidine, 2-(3'-methoxyphenyl)-3-(3''-aminopropyl)thiazolidine, or pharmacologically acceptable salts thereof.

4. The method of making a radioprotective agent comprising reacting a substituted phosphorothioic acid of the formula:

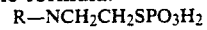

R—NCH$_2$CH$_2$SPO$_3$H$_2$ wherein R is a NH$_2$R' or XNHR' radical in which R' is a C$_2$ to C$_4$ alkyl group and X is a C$_1$ to C$_3$ alkyl group, with an aromatic aldehyde in an alcoholic or dimethylsulfoxide medium at a time and for a temperature sufficient to form a 3-(3"-aminoalkyl)-2-arylthiazolidine having the formula:

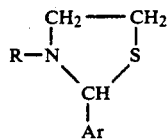

wherein R is a NH$_2$R' or XNHR' radical in which R' is a C$_2$ to C$_4$ alkyl group and X is a C$_1$ to C$_3$ alkyl group and Ar is an aromatic group derived from the corresponding aromatic aldehyde.

5. The method of claim 4 wherein said arylthiazolidine is reacted with an anhydrous acid to form a pharmacologically acceptable salt.

6. The method of claim 4 or 5 wherein said aryl aldehyde is selected from

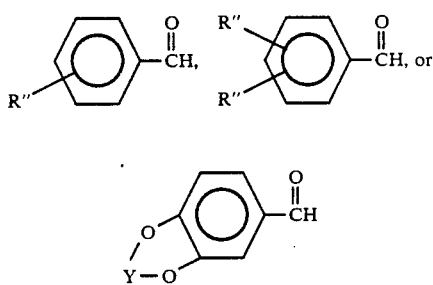

wherein R" is a halogen or nitro group or a C$_1$ to C$_3$ alkoxy, or alkyl radical and Y is a C$_1$–C$_3$ alkylene radical.

7. The method of claim 4 or 5 wherein said substituted phosphorothioic acid is S-(2-(3-aminopropylamino)ethyl phosphorothioate and said aryl aldehyde is selected from

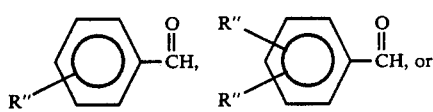

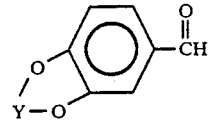

wherein R" is a halogen or nitro group or a C$_1$ to C$_3$ alkoxy, or alkyl radical and Y is a C$_1$–C$_3$ alkylene radical.

8. The method of claim 5 wherein said arylthiazolidine is placed in solution in ether prior to being reacted with said anhydrous acid.

9. The method of protecting an animal against the effects of radioactivity comprising administering to said animal in an amount effective to protect against the effects of radioactivity, a radioprotective agent comprising a 3-(3"-aminoalkyl)-2-arylthiazolidine or a pharmacologically acceptable salt thereof having the formula:

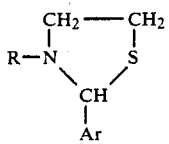

wherein R is a NH$_2$R' or HNHR' radical in which R' is a C$_2$ to C$_4$ alkyl group and X is a C$_1$ to C$_3$ alkyl group and Ar is an aromatic group derived from the corresponding aromatic aldehyde.

10. The method of claim 9 wherein said aromatic aldehyde is selected from

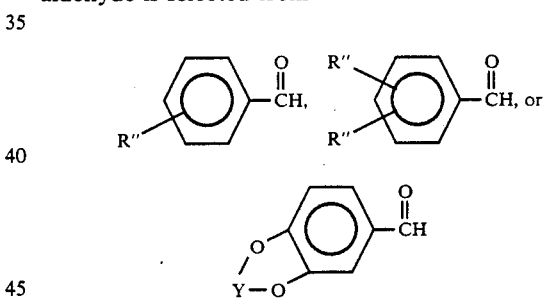

wherein R" is a halogen or nitro group, C$_1$ to C$_3$ alkoxy, or C$_1$ to C$_3$ alkyl radical, and Y is a C$_1$–C$_3$ alkylene radical.

11. The method of claim 9 or 10 wherein said arylthiazolidine is selected from 2-(4'-nitrophenyl)3-(3"-aminopropyl)thiazolidine, 2-(4'-methoxyphenyl)-3-(3'-aminopropyl)thiazolidine, 2-(3',4'-dimethoxyphenyl)-3-(3"-aminopropyl)thiazolidine, 2-[3',4'(methylenedioxy)-phenyl]-3-(3"-aminopropyl)thiazolidine, 2-(3'-methoxyphenyl)-3-(3"-aminopropyl)thiazolidine, or pharmacologically acceptable salts thereof.

* * * * *